March 16, 1948. E. S. BOERNER Plant Pat. 789
ROSE PLANT
Filed Jan. 27, 1947
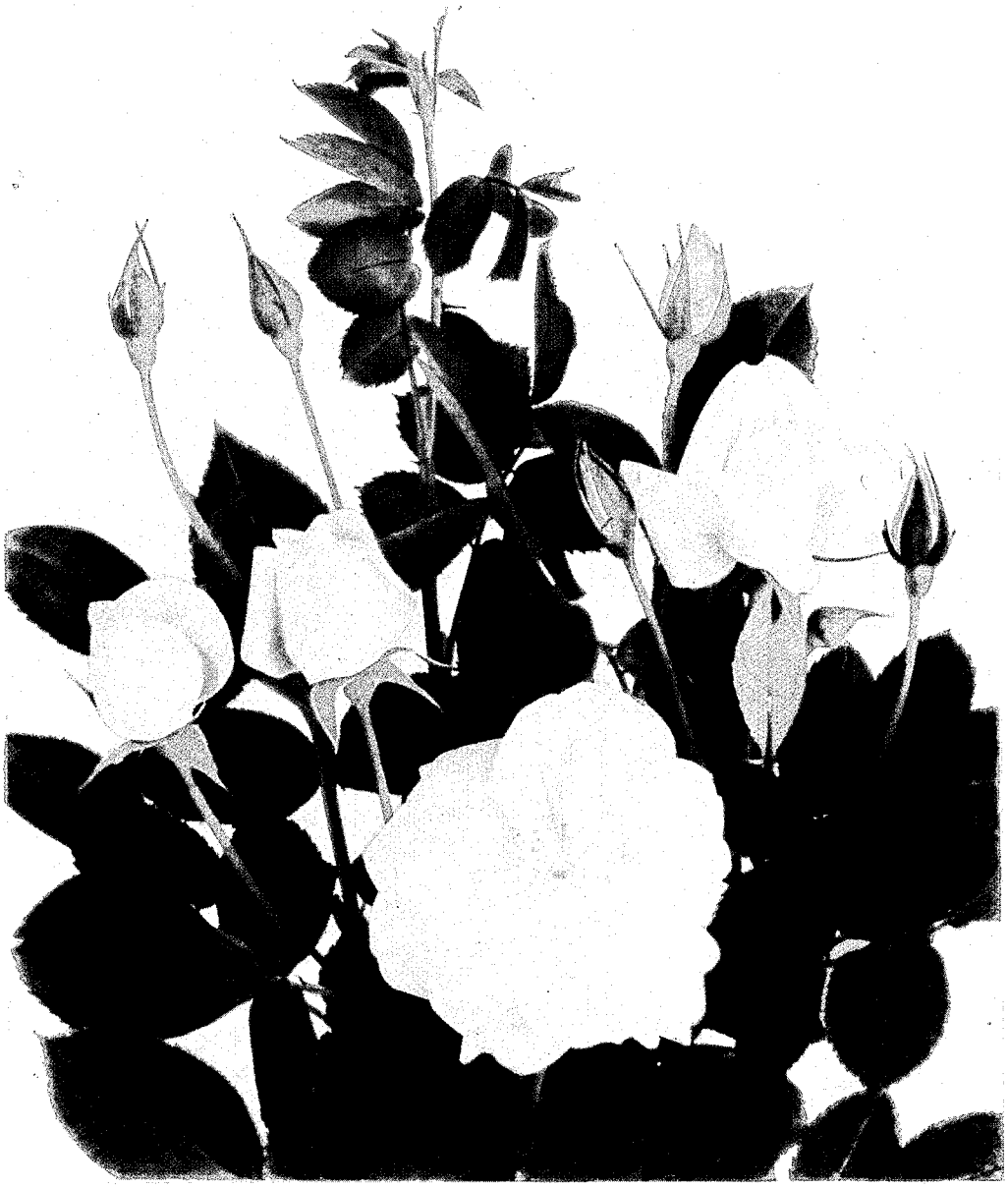
Inventor
E. S. Boerner
By Robbs & Robbs
attorneys Patented Mar. 16, 1948

Plant Pat. 789

UNITED STATES PATENT OFFICE

789

ROSE PLANT

Eugene S. Boerner, Newark, N. Y., assignor to Jackson & Perkins Company, Newark, N. Y., a corporation of New York Application January 27, 1947, Serial No. 724,624

1 Claim. (Cl. 47—61)

The present invention relates to a new and distinct variety of rose plant of the Floribunda class, the important feature of which resides in the distinctiveness of the new color of the flowers in this class of roses, adapting it for decorative purposes in the garden and also for greenhouse growing because of its utility in corsage work and make-up of small, dainty bouquets.

In originating this new rose, I crossed the variety "Pinocchio" (Pl. Pat. #484), a Floribunda type, with the hybrid tea "Crimson Glory" (Pl. Pat. #105), each of which contributed its special characteristics to the present variety, to the extent that the latter is characterized as to novelty by the new color of the bud and the distinguishing color of the flower unlike that of any other rose of which I am aware; by the staunch foliage of the plant; by the distinctive fragrance in a rose of this color much desired in a cut flower variety; by the perfect, high-centered shape of the bloom in miniature, opening up into a very graceful flat flower; and finally, by the habit of the plant of blooming both in large clusters and in individual flowers which give it an effect not found commonly in roses.

Asexual reproduction of this new variety shows the foregoing characteristics come true to form and are established.

In the drawing are shown specimens of the new rose and its foliage at different stages of development of the same.

The following is a detailed description of the new variety, color terminology being in accord with Ridgway's Color Standard:

Parentage: Seedling.
- *Seed parent.*—"Pinocchio."
- *Pollen parent.*—"Crimson Glory."

Classification:
- *Botanic.*—Large flowered polyantha.
- *Commercial.*—Floribunda.

*Flower*

(Observations made in the fields of Jackson & Perkins Company, Newark, New York, in the month of November.)

Blooming habit: Recurrent—continuous.

Bud:
- *Size.*—Medium.
- *Form.*—Pointed. Is not affected by wet or hot weather.
- *Color.*—When sepals first divide—Congo Pink, Plate 28; when petals begin to unfurl—Scarlet, Plate 1; when half blown— inside of petals, Peach Red, Plate 1, overcast with Geranium Pink, Plate 1; reverse of petals, Geranium Pink, Plate 1.
- *Sepals.*—Branched. Curl back when petals begin to unfurl. *Color*—outside—Lettuce Green, Plate 5; inside—Light Lumiere Green, Plate 17.
- *Calyx.*—Shape—pear. Size—small. Aspect—smooth. Color—Biscay Green, Plate 17. Odor when rubbed—none.
- *Peduncle.*—Length—medium. Aspect—rough. Color—Lettuce Green, Plate 5. Strength—erect; bending; slender.
- *Opening.*—Bud opens up well. Is not affected by adverse weather conditions.

Bloom:
- *Size.*—Medium. Average size when fully expanded, 3½".
- *Borne.*—Singly and in clusters. Clusters—irregular.
- *Stems.*—Medium length; strong.
- *Form.*—When first open—high center. Permanence—retains its form to the end.
- *Petalage.*—Double (full but open center). Number of petals under normal conditions, 25.
- *Color.*—Center of flower—Strawberry Pink, Plate 1, overcast with Geranium Pink, Plate 1. Outer petals—Geranium Pink, Plate 1. Base of petals (aiglet)—Sulphur Yellow, Plate 5. Inside of petals—Geranium Pink, Plate 1 overcast with Strawberry Pink, Plate 1. Reverse of petals—Geranium Pink, Plate 1, overcast with Hermosa Pink, Plate 1. General tonality from a distance—Geranium Pink, Plate 1, with Strawberry Pink, Plate 1.
- *Discoloration.*—General tonality at end of first day—Strawberry Pink, Plate 1, overcast with Geranium Pink, Plate 1. Second day—Geranium Pink, Plate 1, overcast with La France Pink, Plate 1. Third day—Geranium Pink, Plate 1, overcast with Shrimp Pink, Plate 1.

Petals:
- *Texture.*—Thin. Is not affected by wet or hot weather.
- *Appearance.*—Inside—satiny. Outside—shiny.
- *Form.*—Round.
- *Arrangement.*—Imbricated (regularly arranged shingle-like). Petaloids in center—none.
- *Persistence.*—Drop off cleanly.

*Fragrance.*—Slight. Nature—"Old Rose perfume" (centifolia).

*Lasting quality.*—On the plant and as cut flower—long.

Genital organs:

*Stamens, Anthers.*—Medium size; many. Color—Apricot Yellow, Plate 4. Arrangement—regular around styles.

*Stamens, filaments (threads).*—Medium length. Color—Pale Lemon Yellow, Plate 4.

*Pollen.*—Maize Yellow, Plate 4.

*Styles.*—Bunched; uneven length; short; thin.

*Stigmas.*—Martius Yellow, Plate 4.

*Ovaries.*—All enclosed in calyx.

*Plant*

Form: Bush.

Growth: Vigorous; upright.

Foliage: Five leaflets.

*Size.*—Medium.

*Quantity.*—Normal.

*Color.*—New foliage: upper side—Oil Green, Plate 5; Serrations—Victoria Lake, Plate 1; under side—Oil Green, Plate 5, overlaid with Victoria Lake, Plate 1. Old foliage: upper side—Ivy Green, Plate 31; serrations—Oxblood Red, Plate 1; under side—Rainette Green, Plate 31, overlaid with Oxblood Red, Plate 1.

*Shape.*—Oval pointed.

*Texture.*—Upper side—leathery. Under side—smooth. Ribs and veins—ordinary.

*Edge.*—Serrated (saw toothed).

*Serrations.*—Single; small.

*Leaf stem.*—Vandyke Brown, Plate 28. Under side—smooth.

*Stipules.*—Medium length; bearded.

*Disease resistance.*—Resistant.

Wood:

*New wood.*—Oxblood Red, Plate 1. Bark—smooth.

*Old wood.*—Cress Green, Plate 31. Bark—smooth.

Thorns:

*Thorns.*—On main stalks from base and on laterals from stalk—ordinary. Form—narrow; short; hooked downward. Color when young—Carmine, Plate 1. Position—irregular.

*Prickles.*—None.

*Hairs.*—None.

I claim:

A new and distinct variety of rose plant characterized as to novelty by the color of the bud and flower; the distinctive fragrance of the cut flowers; the perfect high-centered shape in miniature and opening up into graceful flat flowers; the habit and unique effect of blooming both in large clusters and in individual flowers; and the staunch nature of the foliage, substantially as shown and described.

EUGENE S. BOERNER.